United States Patent [19]

Pensak

[11] 4,118,471

[45] Oct. 3, 1978

[54] STABLE DENTIFRICE

[75] Inventor: Philip Pensak, New Brunswick, N.J.

[73] Assignee: Colgate-Palmolive Company, New York, N.Y.

[21] Appl. No.: 804,958

[22] Filed: Jun. 9, 1977

[51] Int. Cl.² .................. A61K 7/18; B65D 81/24; B65D 81/26; B65D 85/14

[52] U.S. Cl. .................. 424/52; 206/277; 206/524.4; 424/49

[58] Field of Search .................. 424/49–58; 206/277, 524.4

[56] References Cited

U.S. PATENT DOCUMENTS

| | | | |
|---|---|---|---|
| 3,662,060 | 5/1972 | Clippingdale et al. | 424/57 |
| 3,678,155 | 7/1972 | Clippingdale et al. | 424/49 X |
| 4,036,950 | 7/1977 | Baines et al. | 424/57 |

OTHER PUBLICATIONS

Windholz et al., Merck Index, 9th Ed. (1976) p. 1077, Entry 8070, "Saccharin," Entry 8071, Saccharin Soluble Merck & Co., Rahway, N.J.

*Primary Examiner*—Shep K. Rose
*Attorney, Agent, or Firm*—Herbert S. Sylvester; Murray M. Grill; Robert L. Stone

[57] ABSTRACT

A dentifrice which is stable in an unlined aluminum tube comprising alpha-alumina trihydrate polishing agent and which has a pH of about 6.5–8.0, which dentifrice contains an acidifying agent consisting essentially of saccharin acid.

5 Claims, No Drawings

STABLE DENTIFRICE

This invention relates to a dentifrice which is stable in and compatible with an unlined aluminum surface, such as is typically employed as a dentifrice package material, e.g., an aluminum toothpaste tube. In particular the dentifrice contains alpha-alumina trihydrate as a polishing agent.

A conventional way of manufacturing alpha-alumina trihydrate is by the Bayer process. In that process alpha-alumina trihydrate is precipitated from a solution of sodium aluminate. See Encyclopedia of Chemical Technology, Kirk-Othmer, 2nd Edition, Volume 1, pages 937-941 and Volume 2, pages 41-45, 50-51. The alpha-alumina trihydrate is precipitated in the form of granules or agglomerates which are too large for general use as a dentifrice abrasive, e.g., about 40-100 microns diameter. Therefore, the granules or agglomerates after drying (sometimes after water-washing and drying) are ground to a suitable particle size, e.g., to an average particle diameter in the range of about 2 to about 20 microns, such as 5 to 10 microns diameter.

The washed, unground granules usually show an alkaline reaction when slurried in water. For instance, depending on the degree of washing before drying, the pH of a 10% or 20% by weight of alpha-alumina trihydrate slurry at room temperature may be in the range from about 7.5 to 8.5, 9 or 9.5.

The pH can be measured with an Orion model 801 Digital pH/mv meter which is fitted with an EIL model 1150 Combination pH and reference electrode. The instrument is first calibrated at room temperature by placing the electrode into 50 ml of pH buffer solution in a 100 ml breaker and adjusting the calibration control until the instrument reading corresponds to the buffer pH. The electrode is then removed, washed with deionised water and placed into 125g of a prepared 20% slurry of the alpha-aluminate trihydrate sample in deionized water, in a 250 ml breaker, and its pH reading taken.

On grinding, the alkalinity, thus measured increases and the pH measured (as above) of the ground, unwashed, material is generally above 8. For instance, the pH on grinding may change as follows: 7.5 (before grinding) to 8.8 (after grinding); 8.8 (before) to 9.2 (after).

When toothpaste formulations containing highly alkaline milled Bayer process alpha-alumina trihydrates are packed in unlacquered aluminum tubes they react with the aluminium walls of the tube to form gas on storage, even when the pH of the toothpaste is substantially neutral, e.g., 7.1.

It has been proposed in U.S. Pat. Nos. 3,662,060 and 3,678,155 to avoid attack on aluminum by including in the dentifrice containing alpha-alumina trihydrate, phosphate ions or monofluorophosphate ions.

It is noteworthy that reduction in pH in these patents is accomplished with benzoic acid and that specific control formulations therein are disclosed as containing 55% by weight of milled alpha-alumina trihydrate and 0.15% by weight benzoic acid and as having a pH of 6.4.

It is an advantage of this invention that a dentifrice containing alpha-alumina trihydrate polishing material is stable in contact with an unlined aluminum surface when the pH of the dentifrice is between about 6.0-8.0 and the dentifrice contains an acidifying agent consisting essentially of saccharin acid. Such dentifrice does not require the presence of an additional component to provide stability to an unlined aluminum tube surface. Other advantages will be apparent from consideration of the following specification.

In accordance with certain of its aspects this invention relates to a packaged dentifrice comprising an aluminum tube having no inner lining on the aluminum surface and a dentifrice in said tube which comprises a polishing agent of alpha-alumina trihydrate and an acidifying agent consisting essentially of saccharin acid, wherein said dentifrice has a pH of about 6.0-8.0.

Suitable examples of alpha-alumina trihydrate are used usually in the form of fine particles of any desired particle size in the manufacture of the dentifrice. In practice, it is preferred to use the alpha trihydrate form of which at least about 90% of the particles are milled to pass through on a U.S. standard No. 325 mesh sieve and not more than about 5% of the particles by weight are less than 5 microns. Desirable grades of alpha-alumina trihydrate are available from Alcoa of the United States typically as C-333, British Aluminum Co. of Great Britain, typically as Baco AF-260 and Showa Denka of Japan, typically as Higilite H-32.

The dentifrice employed in the present invention is typically a dental cream which has a consistency suitable for extrusion from the aluminum tube. It contains a polishing material typically in amount of about 20-75% by weight. From a major amount (i.e., at least 50%) to all of the polishing material is alpha-alumina trihydrate. When additional polishing agent is present in minor amount of the entire polishing material, it is a water-insoluble agent such as known in the art. It should be present in such amount that the dentifrice remains compatible with the aluminum tube surface. For instance, insoluble alkali metal metaphosphate, such as insoluble sodium metaphosphate and alkaline earth metal carbonate such as calcium carbonate would typically be employed in amounts typically up to about 5% by weight of the dentifrice. Other polishing agents such as dicalcium phosphate (dihydrate and anhydrous), dimagnesium phosphate (trihydrate and anhydrous), tricalcium phosphate, calcium pyrophosphate and polishing grades of silica and sodium aluminosilicate may be present in greater amount.

Saccharin acid is the sulfonated imide of phthalic acid. Thus, it has the formula

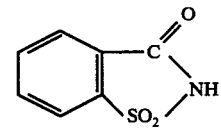

It has a sweetening power similar to that of its sodium salt, but since it is substantially water-insoluble (i.e., it has low water-solubility) while the sodium salt is highly water-soluble, the sodium salt has generally been used in commercial products such as beverages and foods. In dentifrices too, since the sodium salt of saccharin acid can be mixed with gelling agent and then easily dissolved into the liquid phase of the dental cream, the sodium salt is generally employed.

However, this invention utilizes the less water-soluble saccharin acid as an acidifying agent which stabilizes dentifrices containing alpha-alumina trihydrate in contact with unlined aluminum surface. The saccharin acid can be incorporated into a dental cream dentifrice by mixing with the gelling agent and then dispersing it into the liquid phase of the dental cream. It can dissolve to the extent of its limited solubility. It is employed in amount to provide the dentifrice with a pH of about 6.0 to 8.0. Typical amounts may be about 0.1–3% by weight preferably about 0.15–0.25%, about 0.2% being most preferred. Of course, its presence also sweetens the dentifrice and may limit the maximum amount and minimize pH in order not to make the product too sweet.

There are materials other than alpha-alumina trihydrate which have been used in dentifrices which tend to render them corrosive to an unlined aluminum surface, at least in the absence of a stabilizing additive. Such materials should be omitted or present in very small amount. Thus, U.S. Pat. No. 3,878,938 discloses chloroform as such a material. Thus, chloroform, a relatively volatile material which boils below 62° C., although commonly used to modify dentifrice flavor, is preferably not present in the dentifrice of this invention or if present only in such amount as would not corrode aluminum, e.g., less than 0.5% by weight.

Any suitable surface active or detersive material may be included in the dentifrice compositions. Such compatible materials are desirable to provide additional detersive, foaming and antibacterial properties depending upon the specific type of surface active material and are selected similarly. These detergents are water-soluble compounds usually, and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulfate, higher alkyl sulfate (e.g., sodium lauryl sulfate), alkyl aryl sulfonate (e.g., sodium dodecyl benzene sulfonate, higher fatty acid esters of 1,2-dihydroxy propane sulfonate) and the like.

The various surface active materials may be used in any suitable amount, generally from about 0.05 to about 10% by weight, and preferably from about 0.5 to 5% by weight of the dentifrice composition.

It is a further embodiment of the present invention to use the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine N-lauroyl sarcoside, N-lauroyl sarcosine, and sodium N-lauroyl glycide and alanine. For convenience herein, reference to "amino carboxylic acid compound," "sarcoside," and the like refers to such compounds having a free carboxylic group or the water-soluble carboxylic salts.

In dental cream formulations, the liquids and solids should be proportioned to form an extrudible creamy mass of desirable consistency. In general, liquids in the dental cream will comprise chiefly water, glycerine, sorbitol solution, propylene glycol, or the like, including suitable mixtures thereof. It is advantageous usually to use a mixture of both water and a humectant or binder such as glycerine or sorbitol. It is preferred to use glycerine. The total liquid content will generally be about 20–75% by weight of the formulation. It is preferred to use also a gelling agent in dental creams such as the natural and synthetic gum and gum-like material, e.g., Irish moss, gum tragacanth, sodium carboxymethylcellulose, polyvinylpyrroilidone, starch and the like. The Irish moss and sodium carboxymethylcellulose are compatible particularly and are preferred gelling agents as illustrated. The gum content is usually in an amount up to about 10% and preferably about 0.5%–5% by weight of the formulation.

The saccharin acid is typically mixed with the gelling agent during preparation of the dentifrice.

The compositions of the present invention suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2KF$), sodium hexafluorostannate, stannous chlorofluoride, sodium fluorozirconate, and sodium monofluorophosphate. These materials which dissociate or release fluorine containing ions in water, suitably may be present in an effective but non-toxic amount, usually within the range of about 0.01 to 1% by weight of the water soluble fluorine content thereof.

The preferred fluorine-containing compound is sodium monofluorophosphate, typically present in amount of 0.076–7.6% by weight, preferably about 0.76%. It is a particular advantage of this invention that the retention of soluble monofluorophosphate as fluoride is substantially increased in a dentifrice containing saccharin acid and alpha-alumina trihydrate polishing agent over the level retained when sodium saccharin is employed in such a dentifrice with another acidifying agent, such as benzoic acid.

Various materials may be incorporated in the oral preparations of this invention. Examples thereof are coloring or whitening agents, preservatives such as sodium benzoate, silicones, chlorophyll compounds and ammoniated materials such as urea, diammonium phosphate and mixtures thereof. These adjuvants are incorporated in the instant compositions in amounts which do not substantially adversely affect the properties and characteristics suitably selected and used in proper amount depending upon the particular type of preparation involved.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl)-$N^5$-(2,4-dichlorobenzyl)biguanide;
p-chlorophenyl biguanide;
4-chlorobenzyhydryl biguanide;
4-chlorobenzhydrylguanylurea;
N-3-lauroxypropyl-$N^5$-p-chlorobenzylbiguanide;
1,6-di-p-chlorophenylbiguanidehexane;
1-(lauryldimethylammonium)-8-(p-chlorobenzyldimethylammonium) octane dichloride;

5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
and their non-toxic acid addition salts.

Any suitable flavoring may be employed in formulating a flavor for the compositions of the present invention. Suitable flavors are less volatile than chloroform. Examples of suitable flavoring constituents include the flavoring oils, e.g., oils of spearmint, peppermint, wintergreen, sassafras, clove, sage, eucalyptus, marjoram, cinnamon, lemon and orange, as well as methylsalicylate. Saccharin acid provides sweetening to the dentifrice. If desired, a further sweetener such as agents include sucrose, lactose, maltose, sorbitol, sodium cyclamate, dipeptides of U.S. Pat. No. 3,939,261 and oxathiazin salts of U.S. Pat. No. 3,932,606 may be employed. Suitably, flavor and sweetening agent may together comprise from about 0.01 to 5% weight beyond the amount of saccharin acid.

The dental creams should have a pH of about 6.0 to 8.0, preferably about 6.4 to 7.5. The reference to the pH is meant to be the pH determined directly on the dental cream before it is aged. As mentioned, the pH is adjusted with saccharin acid.

The following specific examples are further illustrative of the nature of the present invention, but it is to be understood that the invention is not limited thereto. The compositions are prepared in the usual manner and all amounts of the various ingredients are by weight unless otherwise specified.

EXAMPLE 1

The following dental creams are prepared by dispersing a pre-mix of sodium carboxymethyl cellulose, sodium saccharin or saccharin acid and sodium benzoate into the glycerine, adding the water while mixing to form a gel and adding in turn the alpha-alumina trihydrate, flavor and the sodium lauryl sulfate; then deaerating and placing in aluminum tubes having no inner lining. The dental creams have the following formulas:

| Components | Parts A | Parts B |
| --- | --- | --- |
| Glycerine | 20.202 | 20.202 |
| Sodium carboxymethyl cellulose | 1.1 | 1.1 |
| Sodium saccharin | 0.2 | — |
| Saccharin acid | — | 0.2 |
| Sodium benzoate | 0.5 | 0.5 |
| Water (distilled) | 23.698 | 23.698 |
| Alpha-alumina trihydrate (Alcoa C-333) | 52.0 | 52.0 |
| Sodium lauryl sulfate | 1.5 | 1.5 |
| Flavor (peppermint-spearmint) | 0.8 | 0.8 |
| pH | 8.6 | 6.4 |

The tubes are aged in an oven at 49° C. and removed, cooled and examined after 3, 6 and 9 weeks. The tubes of dental cream A are swollen at 3, 6 and 9 weeks while those of dental cream B are in good condition, thereby indicating superior compatibility of dental cream B (containing saccharin acid) with an aluminum surface over dental cream A (containing sodium saccharin).

Likewise when 0.76 parts of sodium monofluorophosphate replace a like amount of water to form dental cream A' and B', it is observed upon aging for 3, 6 and 9 weeks at 49° C., dental cream A' (with sodium saccharin) reveals evidence of puffing the tubes while dental cream B' (with saccharin acid) and its tubes remain in good condition. The initial pH of dental cream A' is 8.91 and that of dental cream B' is 7.26.

EXAMPLE 2

The following dental creams are prepared, deaerated and placed in unlined aluminum tubes:

| Components | C | D | E | F |
| --- | --- | --- | --- | --- |
| Glycerine | 23.050 | 20.202 | 20.202 | 6.000 |
| Sorbitol (70%) | — | — | — | 16.000 |
| Sodium carboxymethyl cellulose | 1.0 | 1.1 | 1.1 | 1.1 |
| Benzoic acid | 0.33 | 0.33 | — | — |
| Sodium saccharin | 0.2 | 0.2 | — | — |
| Saccharin acid | — | — | 0.2 | 0.2 |
| Sodium monofluorophosphate | 0.76 | 0.76 | 0.76 | 0.76 |
| Water (distilled) | 19.76 | 23.108 | 23.438 | 21.64 |
| Alpha-alumina trihydrate (Alcoa C-333) | 52.0 | 52.0 | 52.0 | 52.0 |
| Sodium lauryl sulfate | 1.5 | 1.5 | 1.5 | 1.5 |
| Flavor (peppermint and spearmint) | 0.8 | 0.8 | 0.8 | 0.8 |
| pH | 6.40 | 5.83 | 7.21 | 6.96 |

Upon aging for 9 weeks at 49° C. dental creams E and F (with saccharin acid) compared to dental creams C and D (with sodium saccharin) have improved retention of soluble monofluorophosphate as fluoride as is shown in the following Table:

| Dental Cream | 49° C - % soluble monoflourophosphate as flouride | | |
| --- | --- | --- | --- |
|  | 3 weeks | 6 weeks | 9 weeks |
| C | 0.040 | 0.030 | 0.023 |
| D | 0.034 | 0.025 | 0.021 |
| E | 0.063 | 0.056 | 0.050 |
| F | 0.076 | 0.069 | 0.068 |

EXAMPLE 3

The following dental creams are prepared, deaerated and placed in unlined aluminum tubes:

| Components | G | H |
| --- | --- | --- |
| Glycerine | 20.202 | 20.202 |
| Sodium carboxymethyl cellulose | 1.1 | 1.1 |
| Sodium saccharin | 0.2 | — |
| Saccharin acid | — | 0.2 |
| Benzoic acid | 0.33 | — |
| Sodium benzoate | — | 0.33 |
| Sodium monofluorophosphate | 0.76 | 0.76 |
| Water (Distilled) | 23.108 | 23.108 |
| Alpha-alumina trihydrate (Showa Denka-Higilite H-32) | 52.0 | 52.0 |
| Sodium lauryl sulfate | 1.5 | 1.5 |
| Flavor (peppermint and spearmint | 0.8 | 0.8 |
| pH | 5.86 | 7.51 |

Upon aging at 49° C. for up to 9 weeks dental cream H (with saccharin acid) is superior in retention of soluble monofluorophosphate as fluoride, compared with dental cream G (with sodium saccharin) the following results being observed:

| Dental Cream | 49° C - % soluble monoflourophosphate as fluoride | | |
| --- | --- | --- | --- |
|  | 3 weeks | 6 weeks | 9 weeks |
| G | 0.048 | 0.038 | 0.033 |
| H | 0.065 | 0.053 | 0.048 |

It will be apparent to one skilled in the art that modification of dental creams B, B', E, F and H can be made.

I claim:

1. A packaged dentifrice comprising an aluminum tube having no inner lining on the aluminum surface and a dentifrice in said tube comprising an aqueous liquid and solids proportioned to an extrudible creamy mass and dispersed therein a polishing agent of alpha-alumina trihydrate, a fluorine-containing compound in amount to provide about 0.01–1% by weight of fluorine-containing ions and an acidifying agent consisting essentially of saccharin acid, wherein said dentifrice has a pH of about 6.5–8.0.

2. The packaged dentifrice claimed in claim 1 wherein said alpha-alumina trihydrate is present in major amount by weight of said polishing agent and said polishing agent comprises about 20–75% by weight of said dentifrice.

3. The packaged dentifrice claimed in claim 2 wherein said dentifrice has a pH of about 6.6–7.5.

4. The packaged dentifrice claimed in claim 3 wherein said dentifrice contains about 0.2% of saccharin acid.

5. The packaged dentifrice claimed in claim 1 wherein said fluorine-containing compound is sodium monofluorophosphate.

* * * * *